US011559530B2

(12) United States Patent
Chidambaram et al.

(10) Patent No.: US 11,559,530 B2
(45) Date of Patent: Jan. 24, 2023

(54) ORAL TESTOSTERONE UNDECANOATE THERAPY

(71) Applicant: Lipocine Inc., Salt Lake City, UT (US)

(72) Inventors: Nachiappan Chidambaram, Sandy, UT (US); Satish Kumar Nachaegari, Holladay, UT (US); Mahesh V. Patel, Salt Lake City, UT (US); Kilyoung Kim, Salt Lake City, UT (US)

( * ) Notice: Subject to any disclaimer, the term of this patent is extended or adjusted under 35 U.S.C. 154(b) by 0 days.

(21) Appl. No.: 15/825,019

(22) Filed: Nov. 28, 2017

(65) Prior Publication Data
US 2018/0333422 A1    Nov. 22, 2018

Related U.S. Application Data

(60) Provisional application No. 62/442,612, filed on Jan. 5, 2017, provisional application No. 62/428,336, filed on Nov. 30, 2016, provisional application No. 62/427,103, filed on Nov. 28, 2016.

(51) Int. Cl.
*A61K 31/568* (2006.01)
*A61P 5/26* (2006.01)
*A61K 9/48* (2006.01)
*A61K 9/00* (2006.01)
*A61K 31/575* (2006.01)

(52) U.S. Cl.
CPC .......... *A61K 31/568* (2013.01); *A61K 9/0053* (2013.01); *A61K 9/48* (2013.01); *A61K 9/4858* (2013.01); *A61K 31/575* (2013.01); *A61P 5/26* (2018.01)

(58) Field of Classification Search
CPC .. A61K 31/568; A61K 9/0053; A61K 9/4858; A61K 9/48; A61K 31/575; A61P 5/26
See application file for complete search history.

(56) References Cited

U.S. PATENT DOCUMENTS

| | | | |
|---|---|---|---|
| 2,680,749 A | 6/1954 | Cawley et al. |
| 2,742,487 A | 4/1956 | Robledano |
| 3,097,139 A | 7/1963 | Thorp |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | Van der Vies |
| 4,147,783 A | 4/1979 | Van der Vies |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | Van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,689,333 A | 8/1987 | Nohara et al. |
| 4,695,450 A | 9/1987 | Bauer |
| 4,703,042 A | 10/1987 | Bodor |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |
| 4,874,795 A | 10/1989 | Yesair |
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |

(Continued)

FOREIGN PATENT DOCUMENTS

| | | |
|---|---|---|
| CA | 2295028 A1 | 1/1999 |
| CA | 2302735 A1 | 1/2000 |

(Continued)

OTHER PUBLICATIONS

Yin, Reexamination of Pharmacokinetics of Oral Testosterone Undecanoate in Hypogonadal Men With a New Self-Emulsifying Formulation, J. Androl., 2012, 33(2), pp. 1-19 (Year: 2012).*

Dandona et al.; "A practical guide to male hypogonadism in the primary care setting"; The International Journal of Clinical Practice; (May 2010); pp. 682-696; vol. 64, No. 6; <doi: 10.1111/j.1742-1241.2010.02355.x >.

Kaminetsky et al.; PD37-08 Efficacy and Pharmacokinetics of LPCN 1021, A Novel Oral Testosterone Replacement Therapy (TRT), in Hypogonadal Men: Study of Androgen Replacement (SOAR); The Journal of Urology®; (May 18, 2015); 1 page; vol. 193, No. 4S, Supplement.

NIH; "History of Changes for Study: NCT02081300, Safety and Efficacy of Oral LPCN 1021 in Men With Low Testosterone or Hypogonadism"; Archive History for NCT02081300; (Mar. 5, 2014); 10 pages; retrieved on Apr. 30, 2018; [Retrieved from <URL: https://clincialtrials.gov/ct2/history/NCT02081300?V >].

(Continued)

*Primary Examiner* — Savitha M Rao
*Assistant Examiner* — Andrew P Lee
(74) *Attorney, Agent, or Firm* — Michael R. Schramm

(57) ABSTRACT

The present disclosure provides methods and compositions for testosterone replacement therapy. The methods and compositions employ a fixed dose dosing regimen that does not require titration or dose adjustments and that can provide a therapeutically effective amount of a testosterone ester while avoiding unacceptably high testosterone levels.

17 Claims, No Drawings

(56) References Cited

U.S. PATENT DOCUMENTS

| | | |
|---|---|---|
| 4,994,439 A | 2/1991 | Longenecker et al. |
| 5,023,108 A | 6/1991 | Bageria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,104,656 A | 4/1992 | Seth et al. |
| 5,120,710 A | 6/1992 | Liedtke |
| 5,140,021 A | 8/1992 | Maxon et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List et al. |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahashi et al. |
| 5,962,014 A | 10/1999 | Hauer et al. |
| 5,962,017 A | 10/1999 | Hauer et al. |
| 5,965,161 A | 10/1999 | Oshlack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |

(56) References Cited

U.S. PATENT DOCUMENTS

| | | |
|---|---|---|
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Pope |
| 6,667,048 B1 | 12/2003 | Lambert et al. |
| 6,692,766 B1 | 2/2004 | Rubinstein et al. |
| 6,696,482 B2 | 2/2004 | Schenoy et al. |
| 6,720,001 B2 | 4/2004 | Chen et al. |
| 6,737,082 B1 | 5/2004 | Picornell Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,913,244 B1 | 7/2005 | Atkinson et al. |
| 6,923,988 B2 | 8/2005 | Patel et al. |
| 6,977,083 B1 | 12/2005 | Huebier et al. |
| 6,982,281 B1 | 1/2006 | Chen et al. |
| 7,025,979 B2 | 4/2006 | Neischlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 8/2012 | Dudley et al. |
| 8,338,395 B2 | 12/2012 | Hubler et al. |
| 8,778,916 B2 | 7/2014 | Dudley et al. |
| 8,778,922 B2 | 7/2014 | Giliyar et al. |
| 8,865,695 B2 | 10/2014 | Giliyar et al. |
| 9,034,858 B2 | 5/2015 | Giliyar et al. |
| 9,205,057 B2 | 10/2015 | Giliyar et al. |
| 9,358,241 B2 | 6/2016 | Giliyar et al. |
| 9,498,485 B2 | 6/2016 | Patel et al. |
| 9,480,690 B2 | 11/2016 | Giliyar et al. |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwarz |
| 2002/0103139 A1 | 8/2002 | Weisspapir et al. |
| 2002/0183296 A1 | 12/2002 | Dudley et al. |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0216360 A1 | 11/2003 | Grawe et al. |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0127476 A1 | 7/2004 | Kershaman et al. |
| 2005/0031693 A1 | 2/2005 | Babcock et al. |
| 2005/0032762 A1 | 2/2005 | Hubler et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | De Nijs et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0154533 A1 | 7/2007 | Dudley |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2008/0317859 A1 | 12/2008 | Soumac et al. |
| 2009/0074859 A1 | 3/2009 | Patel |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1 | 7/2010 | Giliyar et al. |
| 2011/0039814 A1 | 2/2011 | Huatan et al. |
| 2011/0142945 A1 | 6/2011 | Chen et al. |
| 2011/0160168 A1 | 6/2011 | Dhingra |
| 2011/0251167 A1 | 10/2011 | Dudley et al. |
| 2011/0263552 A1 | 10/2011 | Dhingra et al. |
| 2012/0135074 A1 | 5/2012 | Giliyar et al. |
| 2012/0148675 A1 | 6/2012 | Chickmath et al. |
| 2012/0244215 A1 | 9/2012 | Gilyar et al. |
| 2012/0309731 A1 | 12/2012 | Dudley et al. |
| 2012/0322780 A1 | 12/2012 | Giliyar et al. |
| 2013/0022674 A1 | 1/2013 | Dudley et al. |
| 2013/0023505 A1 | 1/2013 | Garfield et al. |
| 2013/0052263 A1 | 2/2013 | Fikstad et al. |
| 2013/0178454 A1 | 7/2013 | Bhasin et al. |
| 2013/0225544 A1 | 8/2013 | Nachaegari et al. |
| 2014/0178466 A1 | 6/2014 | Giliyar et al. |
| 2014/0179652 A1 | 6/2014 | Giliyar et al. |
| 2014/0303130 A1 | 10/2014 | Giliyar et al. |
| 2014/0309202 A1 | 10/2014 | Giliyar et al. |
| 2015/0038475 A1 | 2/2015 | Chickmath et al. |
| 2015/0064243 A1 | 3/2015 | Chen et al. |
| 2015/0224059 A1 | 8/2015 | Giliyar |
| 2015/0273067 A1 | 10/2015 | Patel |
| 2015/0320765 A1 | 11/2015 | Giliyar et al. |
| 2016/0074416 A1 | 3/2016 | Giliyar et al. |
| 2016/0184321 A1 | 6/2016 | Patel et al. |
| 2016/0184324 A1 | 6/2016 | Patel et al. |
| 2016/0193225 A1 | 7/2016 | Patel |
| 2016/0317553 A1 | 11/2016 | Salameh et al. |
| 2016/0361322 A1 | 12/2016 | Patel |
| 2016/0367569 A1 | 12/2016 | Giliyar et al. |
| 2017/0007622 A1 | 1/2017 | Giliyar et al. |
| 2017/0056415 A1 | 3/2017 | Patel et al. |

FOREIGN PATENT DOCUMENTS

| | | |
|---|---|---|
| CN | 101217963 A | 7/2008 |
| DE | 2508615 A1 | 9/1975 |
| DE | 10108614 A1 | 9/2002 |
| EP | 0036145 B1 | 5/1985 |
| EP | 0184942 A2 | 6/1986 |
| EP | 0537070 A1 | 4/1993 |
| EP | 0724877 A1 | 8/1996 |
| EP | 0981328 A1 | 3/2000 |
| EP | 0988858 A1 | 3/2000 |
| EP | 1 103252 A1 | 5/2001 |
| EP | 0904064 B1 | 10/2001 |
| EP | 1624855 A2 | 2/2006 |
| EP | 1879456 A1 | 1/2008 |
| EP | 2000130 A1 | 12/2008 |

(56) References Cited

FOREIGN PATENT DOCUMENTS

| | | |
|---|---|---|
| EP | 2558073 B1 | 9/2014 |
| FR | 2647346 B1 | 9/1991 |
| FR | 2758459 A1 | 7/1998 |
| GB | 1264677 A | 2/1973 |
| GB | 2098865 A | 12/1982 |
| GB | 2228198 A | 8/1990 |
| JP | S52/66616 A | 6/1977 |
| JP | S52/148060 A | 12/1977 |
| JP | S57/70824 A | 5/1982 |
| JP | H01/139526 A | 6/1989 |
| JP | H05/194209 A | 8/1993 |
| JP | 07041422 A | 2/1995 |
| JP | H07/508724 A | 9/1995 |
| JP | 09241152 A | 9/1997 |
| JP | 11049664 A | 2/1999 |
| JP | 11152227 A | 6/1999 |
| JP | 2001/500368 A | 1/2001 |
| JP | 2001/508445 A | 6/2001 |
| JP | 2001/514626 A | 9/2001 |
| JP | 2002/510311 A | 4/2002 |
| JP | 2002/520377 A | 7/2002 |
| JP | 2003/500368 A | 1/2003 |
| JP | 2005/500347 A | 1/2005 |
| JP | 2008/537960 A | 10/2008 |
| JP | 2008/540451 A | 11/2008 |
| WO | WO 82/01649 A1 | 5/1982 |
| WO | WO 84/02076 A1 | 6/1984 |
| WO | WO 88/00059 A1 | 1/1988 |
| WO | WO 92/18147 A1 | 10/1992 |
| WO | WO 93/02664 A1 | 2/1993 |
| WO | WO 93/06921 A1 | 4/1993 |
| WO | WO 93/25192 A1 | 12/1993 |
| WO | WO 94/08610 A1 | 4/1994 |
| WO | WO 94/25068 A1 | 11/1994 |
| WO | WO 95/01785 A1 | 1/1995 |
| WO | WO 95/01786 A1 | 1/1995 |
| WO | WO 95/24893 A1 | 9/1995 |
| WO | WO 95/34287 A1 | 12/1995 |
| WO | WO 96/17597 A1 | 6/1996 |
| WO | WO 97/04749 A1 | 2/1997 |
| WO | WO 97/40823 A1 | 11/1997 |
| WO | WO 97/48382 A2 | 12/1997 |
| WO | WO 98/00116 A1 | 1/1998 |
| WO | WO 98/30205 A1 | 7/1998 |
| WO | WO 98/33512 A1 | 8/1998 |
| WO | WO 98/38984 A2 | 9/1998 |
| WO | WO 98/50077 A1 | 11/1998 |
| WO | WO 98/56357 A1 | 12/1998 |
| WO | WO 99/00111 A1 | 1/1999 |
| WO | WO 99/29300 A1 | 6/1999 |
| WO | WO 99/40904 A2 | 8/1999 |
| WO | WO 99/44584 A1 | 9/1999 |
| WO | WO 99/48498 A1 | 9/1999 |
| WO | WO 00/003753 A2 | 1/2000 |
| WO | WO 00/016749 A1 | 3/2000 |
| WO | WO 00/025772 A1 | 5/2000 |
| WO | WO 00/037057 A2 | 6/2000 |
| WO | WO 00/050007 A1 | 8/2000 |
| WO | WO 00/057859 A1 | 10/2000 |
| WO | WO 00/057918 A2 | 10/2000 |
| WO | WO 00/059482 A1 | 10/2000 |
| WO | WO 00/059512 A1 | 10/2000 |
| WO | WO 00/071163 A1 | 11/2000 |
| WO | WO 00/072825 A1 | 12/2000 |
| WO | WO 00/076482 A1 | 12/2000 |
| WO | WO 01/001960 A1 | 1/2001 |
| WO | WO 01/012155 A1 | 2/2001 |
| WO | WO 01/021154 A2 | 3/2001 |
| WO | WO 01/028555 A1 | 4/2001 |
| WO | WO 01/037808 A1 | 5/2001 |
| WO | WO 01/049262 A1 | 7/2001 |
| WO | WO 02/039983 A2 | 5/2002 |
| WO | WO 03/068186 A1 | 8/2003 |
| WO | WO 2004/087052 A2 | 10/2004 |
| WO | WO 2004/105694 A2 | 12/2004 |
| WO | WO 2005/041929 A2 | 5/2005 |
| WO | WO 2006/013369 A2 | 2/2006 |
| WO | WO 2006/113505 A2 | 10/2006 |
| WO | WO 2006/119498 A2 | 11/2006 |
| WO | WO 2007/018943 A2 | 2/2007 |
| WO | WO 2007/100614 A2 | 9/2007 |
| WO | WO 2010/081032 A2 | 7/2010 |
| WO | WO 2010/102737 A1 | 9/2010 |
| WO | WO 2011/082384 A2 | 7/2011 |
| WO | WO 2011/129812 A1 | 10/2011 |
| WO | WO 2012/075081 A2 | 7/2012 |

OTHER PUBLICATIONS

Addo et al.; "Non Polar Extracts of Serum From Males Contain Covert Radioimmunoassayable Testosterone"; Steroids; (Sep. 1989); pp. 25-269; vol. 54(3).

Alvarez et al.; "The Role of Calcium Ions and Bile Salts on the Pancreatic Lipase-Catalyzed Hydrolysis of Triglyceride Emulsions Stabilized with Lecithin"; Pharmaceutical Research; (1989); pp. 449-457; vol. 6(6).

ANDRIOL® Testocaps®; Consumer Medicine Information; (Sep. 2003).

ANDRODERM® Product Label and Medication Guide; 1995; Labeler—Watson Pharma, Inc.; Revised Nov. 2013; 23 pages.

ANDROGEL® Product Label and Medication Guide; May 2013; Labeler—AbbVie Inc.; Revised Oct. 2013; 28 pages.

Atkinson et al; "Long Term Experience with Testosterone Replacement Through Scrotal Skin; Testosterone: Action, Deficiency and Substitution"; Nieschlag, E. and Behre, HM, Eds.; (1998); pp. 365-388.

Aungst; "Intestinal Permeation Enhancers," Journal of Pharmaceutical Sciences; (2000); pp. 429-442; vol. 89(4).

Baert et al; "Analytical, biopharmaceutical and regulatory evaluation of topical testosterone preparations"; European Journal of Pharmaceutics and Biopharmaceutics; (2009); pp. 275-281; vol. 72; <doi: 10.1016/j.ejpb.2008.10.014 >.

Bagchus et al.; "Important Effect of Food on the Bioavailability of Oral Testosterone Undecanoate"; Pharmacotherapy; (2003); pp. 319-325; vol. 23(3).

Baluom et al.; "The Importance of Intestinal Residence Time of Absorption Enhancer on Drug Implication on Formulative Considerations"; International Journal of Pharmaceutics; (1998); pp. 21-30; vol. 176.

Bates et al.; "Bioavailability of Micronized Griseofulvin from Corn Oil-in-Water Emulsion, Aqueous Suspension, and Commercial Tablet Dosage Forms in Humans"; Journal of Pharmaceutical Sciences; (1975); pp. 793-797; vol. 64(5).

Beatch et al.; "Ventricular Fibrillation, an Uncontrolled Arrhythmia Seeking New Targets"; Drug Development Research Journal; (2002); pp. 45-52; vol. 55.

Bernkop-Schnurch; "The Use of Inhibitory Agents to Overcome the Enzymatic Barrier to Orally Administered Therapeutic Peptides and Proteins"; Journal of Controlled Release; (Apr. 1998); pp. 1-16; vol. 52(1-2).

Bhargava et al.; "Using Microemulsions for Drug Delivery"; Pharmaceutical Technology; (Mar. 1987); pp. 46-53.

Blystone et al.; "Toxicity and Carcinogenicity of Androstenedione in F344/N Rats and B6C3F2 Mice"; Food and Chemical Toxicology; (Sep. 2011); pp. 2116-2124; <doi: 10.1016/j.fct.2011.05.026. Epub2011May30 >.

BUGAY; "Characterization of the Solid-State: Spectroscopic Techniques"; Advanced Drug Delivery Review; (May 16, 2001); pp. 43-65; vol. 48(1).

Burbello et al.; Sovremennye Lekarstvennyesredstava S-Pb Neva; (2004); p. 567.

Cantrill; "Which Testosterone Replacement Therapy"; Clinical Endocrinology Journal; (1984); pp. 97-107; vol. 21.

Charman et al.; "Physicochemical and Physiological Mechanisms for the Effects of Food on Drug Absorption: The Role of Lipids and pH"; Journal of Pharmaceutical Sciences; (1997); pp. 269-282; vol. 86(3).

(56) References Cited

OTHER PUBLICATIONS

Constantidides; "Lipid Microemulsion for Improving Drug Dissolution and Oral Absorption: Physical and Biopharmaceutical Aspect"; Pharmaceutical Research; (1995); pp. 1561-1572; vol. 12(11).
DEPO-TESTOSTERONE® Product Label and Medication Guide; Sep. 2006; Labeler—Pharmacia & Upjohn Company; Revised Aug. 2013; 12 pages.
Emulsion; IUPAC Compendium of Chemical Terminology, 2nd Ed., 1997.
Frey et al.; "Bioavailability of Oral Testosterone in Males"; European Journal of Pharmacology; (1979); pp. 345-349; vol. 16.
Gennaro; "Surfactant Properties in Solution and Micelle Formation, Colloidal Dispersions"; Remington's Pharmaceutical Sciences; (1985); pp. 293-300; Chapter 20.
Goncharova et al.; "Preparation of Testosterone Esters"; Pharmaceutical Chemistry Journal; (Jul. 1973); pp. 427-428; vol. 7(7).
Gonzalo-Lumbrerars et al.; "HPLC Method Development for Testosterone Propionate and Cipionate in Oil-Based Injectables"; Journal of Pharmaceutical and Biomedical Analysis; (Jul. 15, 2005); pp. 757-762; vol. 38(4).
Gooren; "A Ten-year Safety Study of the Oral Androgen Testosterone Undecanoate"; Journal of Andrology; (1994); pp. 212-215; vol. 15(3).
Grahame-Smith et al; The Oxford Textbook of Clinical Pharmacology and Drug Therapy; (1992); pp. 25, 136-137; $2^{nd}$ Edition; M. Meditsina Publisher; (English version included pp. 9-12, 122-124).
Healthline; "What are the symptoms of Hypogonadism?"; 1 page; [Internet]; [Retrieved on Apr. 1, 2014] [Retrieved from <URL: http://www.healthline.con/health/hypogonadism#Overview1 >].
Hong, B.S., et al.; "Recent trends in the treatment of testosterone deficiency syndrome"; International Journal of Urology; (2007); pp. 981-985; vol. 14; The Japanese Urological Association; <doi: 10.1111/j.1442-2042.2007.01882.X >.
Hörter et al.; "Influence of Physiochemical Properties on Dissolution of Drugs in the Gastrointestinal Tract"; Advanced Drug Delivery Reviews; (1997); pp. 3-14; vol. 25.
Houwing et al.; "Pharmacokinetic Study in Women of Three Different Doses of a New Formulation of Oral Testosterone Undecanoate, Andriol Testocaps", Pharmacotherapy; (2003); pp. 1257-1265; vol. 23(10).
Humberstone et al.; "Lipid-based Vehicles for the Oral Delivery of Poorly Water Soluble Drugs"; Advanced Drug Delivery Reviews; (1997) pp. 103-128.
Hutchison; "Digestible Emulsions and Microemulsions for Optimum Oral Delivery of Hydrophobic Drugs"; Bulletin Technique Gattefosse; (1994); pp. 67-74; vol. 87.
Javanbakht et al.; "Pharmacokinetics of a Novel Testosterone Matrix Transdermal System in Health, Premenopausal Women and Women Infected with the Human Immunodeficiency Virus 1"; Journal of Clinical Endocrinology & Metabolism; (2000); pp. 2395-2401; vol. 85(7).
Johnson; "Gastrointestinal Physiology"; Department of Physiology; University of Texas Medical School; (1997); pp. 25-26, 93-106, 133-134, 136-137; Houston, Texas.
Julien; "A concise nontechnical guide to the actions, uses, and side effects of psychoactive drugs"; A Primer of Drug Action; (2001); pp. 5-6; $9^{th}$ Edition.
Kalinchenko; "Testosterone—King Hormones, hormones kings"; The Journal; Sex and Life; (2004); pp. 12-22; [Retrieved on Mar. 26, 2010]; [Retrieved from <URL: http://www.laz.med.ru/interesting/publications/testosterone.html >].
Köhn et al.; "A New Oral Testosterone Undecanoate Formulation"; World Journal of Urology; (Nov. 2003); pp. 311-315; vol. 21(5); <doi: 10.1007/s00345-003-0372-x >.
Langer; "New Methods of Drug Delivery"; Science; (Sep. 1990); pp. 1527-1533; vol. 249(4976).
Lecluyse et al.; "In Vitro Models for Selection of Development Candidates. Permeability Studies to Define Mechanisms of Absorption Enhancement"; Advanced Drug Delivery Reviews; (1997); pp. 163-183; vol. 23.
Leichtnam et al.; "Testosterone Hormone Replacement Therapy: State-of-the-Art and Emerging Technology"; Pharmaceutical Research; (2006); pp. 1117-1132; vol. 23(6).
LGC; Reference Standard Testosterone Undecanoate; Certificate of Analysis; (Jul. 5, 2015); 6 pages; LGC GmBH; Germany.
Lopez-Berestein et al. (Eds.); Liposomes in the Therapy of Infectious Disease and Cancer; (1989); pp. 353-365; Liss; New York.
Macgregor et al.; "Influence of Lipolysis on Drug Absorption From the Gastro-Intestinal Tract"; Advanced Drug Delivery Reviews; (1997); pp. 33-46; vol. 25.
Maisey et al; "Clinical Efficacy of Testosterone Undecanoate in Male Hypogonadism"; Clinical Endocrinology; (1981); pp. 625-629; vol. 14.
Mcauley et al; "Oral Administration of Micronized Progesterone: A Review and More Experience"; Pharmacotherapy; (May 1996); pp. 453-457; vol. 16(3).
Meinert et al.; Clinical Trials: Design, Conduct and Analysis (Monographs in Epidemiology and Biostatistics; (1986); vol. 8.
Merck Index, "Alpha Tocopherol"; Monograph 09571; (2001-2004); Merck & Co. Inc.
Merck Index; "Amiodarone"; Monograph 504; (1996); p. 84; $12^{th}$ Edition; Merck & Co., Inc.
Merck Index; "Carvedilo"; Monograph 01888; (2001-2004); Merck & Co., Inc.
Merck Index; "Fenofibrate"; Monograph 3978; (2006); pp. 679-680; $14^{th}$ Edition; Merck & Co., Inc.
Merck Index; "Risperidone"; Monograph 08316; (2001-2004); Merck & Co., Inc.
Merck Index; "Shellac"; Monograph 8623; (1996); p. 8526; $12^{th}$ Edition.
Merck Index; "Testosterone"; Monograph 9322; (1996); p. 9326; $12^{th}$ Edition; Merck & Co., Inc.
Merck Index; "Vitamin E" and "Vitamin E Acetate"; Monographs 9931 and 9932; (1989); pp. 1579-1580; $11^{th}$ Edition; Merck & Co., Inc.
Merck Index; "Vitamin E"; Monograph 10021; (2006); p. 1726; $14^{th}$ Edition; Merck & Co., Inc.
Merck Index; "Ziprasidone"; Monograph 10224;(2001-2004); Merck & Co., Inc.
Merriam-Webster Dictionary; "Granule"; [Retrieved Dec. 17, 2009] [Retrieved from <URL: http://www.mw.com/dictionary/granule >].
Mittal et al; "The Wide World of Micelles"; In: International symposium on Micellization, Solubilization, and Microemulsions, $7^{th}$ Northeastern Regional Meeting of the American Society; Albany, New York; (1976); pp. 1-21; vol. 1 <ISBN: 0-306-31023-6(v.1) >.
Moellering; "Vancomycin: A 50-Year Reassessment"; Clinical Infectious Diseases; (2006); pp. S3-S4; vol. 42.
Muranishi; "Absorption Enhancers"; Critical Reviews in Therapeutic Drug Carrier Systems; (1990); pp. 1-33; vol. 7(1).
Muranishi; "Potential Absorption of Heparin from the Small Intestine and the Large Intestine in the Presence of Monoolein Mixed Micelles"; Chemical and Pharmaceutical Bulletin Journal; (1977); pp. 1159-1161; vol. 24(5).
Nieschlag et al.; "Plasma Androgen Levels in Men after Oral Administration of Testosterone or Testosterone Undecanoate"; Acta Endocrinologica; (1975); pp. 366-374; vol. 79(2); (Abstract).
Noguchi et al; "The Effect of Drug Lipophilicity and Lipid Vehicles on the Lymphatic Absorption of Various Testosterone Esters"; International Journal of Pharmaceutics; (May 1985); pp. 173-184; vol. 24(2-3).
Osol (Ed.); "Emulsions"; Remington's Pharmaceutical Sciences; (1975); pp. 327-339, 1452-1456; $15^{th}$ Edition.
Perchersky et al. "Androgen administration in middle-aged and aging men: effects of oral testosterone undecanoate on dihydrotestosterone, oestradiol and prostate volume"; International Journal of Andrology; (2002); pp. 119-125; vol. 25.
Pouton; "Formulation of Self-Emulsifying Drug Delivery Systems"; Advanced Drug Delivery Reviews; (1997); pp. 47-58; vol. 25.
Pozo et al.; "Quantification of Testosterone Undecanoate in Human Hair by Liquid Chromatography-Tandem Mass Spectrometry"; Biomedical Chromatography; (Aug. 2009); pp. 873-880; vol. 23(8).

(56) References Cited

OTHER PUBLICATIONS

Remington; "Surfactant Properties in Solution and Micelle Formation"; The Science and Practice of Pharmacy; (1995); pp. 272-276; (19th Edition).

Reymond et al.; "In Vivo Model for Ciclosporin Intestinal Absorption in Lipid Vehicles"; Pharmaceutical Research; (1988); pp. 677-679; vol. 5(10).

S1 Sec Filing (Securities and Exchange Commission) for Clarus Therapeutics, Inc.; Filed May 23, 2014 with the Securities and Exchange Commission; 207 pages.

Saudek et al.; "A preliminary trial of the programmable implantable medication system for insulin delivery"; The New England Journal of Medicine; (Aug. 31, 1989); pp. 574-579; vol. 321.

Schnabel et al.; "The effect of food composition on serum testosterone levels after oral administration of Andriol Testocaps"; Clinical Endocrinology; (2007); pp. 579-585; vol. 66(4).

Schott; "Comments on Hydrophile-Lipophile Balance Systems"; Journal of Pharmaceutical Sciences; (Jan. 1990); pp. 87-88; vol. 79(1); American Pharmaceutical Association.

sciencelab.com; "MSDS: Glyceryl Monooleate"; Material Safety Data Sheet; (Oct. 2005); 5 pages; <URL: www.sciencelab.com >.

Sefton; "Implantable Pumps"; Critical Reviews in Biomedical Engineering; (1987); pp. 201-240; vol. 14, No. 3; (Abstract); [Sourcelink] <URL: http://www.ncbi.nlm.nih.gov/pubmed/3297487 >.

Seidman et al.; "Testosterone replacement therapy for hypogonadal men with SSRI-refractory depression"; Journal of Affective Disorders; (1998); pp. 157-161; vol. 48.

Shackleford et al., "Contribution of Lymphatically Transported Testosterone Undecanoate to the Systemic Exposure of Testosterone after Oral Administration of two Andriol Formulations in Conscious Lymph Duct-Cannulated Dogs"; The Journal of Pharmacology and Experimental Therapeutics; (2003); pp. 925-933; vol. 306(3).

Shanghai PI Chemicals Ltd.; "MSDS: Testosterone Undecanoate"; Material Safety Data Sheet; (2007); [Retrieved on Jun. 3, 2009] [retrieved from <URL: http://www.pipharm.com/product/msds-13457.pdf >].

Stedman's Medical Dictionary; "Dehydro-e-epiandrosterone"; "Dehydroisoandroteron"; and "Steriod"; (1972); pp. 329, 1195-1197; 22nd Edition; Williams & Wilkins Co.

Stedman's Medical Dictionary; "Hydroxy-Acid and Vitamin E"; (1973); pp. 595, 14000; 22nd Edition; Williams & Wilkins Co.

Stedman's Medical Dictionary; "Surfactants"; (1972); p. 1225; 22nd Edition; Williams & Wilkins Co.

Stedman's Medical Dictionary; "Surfactants"; (2006); 28th Edition; Williams & Wilkins Co.

Swerdloff, et al; "Long Term pharmaceokinetics of transdermal testosterone gel in hypogonadal men". Journal of Clinical Endocrinology & Metabolism; (2000); pp. 4500-4510; vol. 85.

Tarr et al.; "Enhanced Intestinal Absorption of Cyclosporine in Rats Through the Reduction of Emulsion Droplet Size"; Pharmaceutical Research; (1989); pp. 40-43; vol. 6(1).

Tarumi et al.; "Androstenedione induces abnormalities in morphology and function of developing oocytes, which impairs oocyte meiotic competence"; Journal of Fertility and Sterility; (Feb. 2012); pp. 469-476; vol. 97(2); <doi: 10.1016/j.fertnstert.2011.11.040 >.

Tauber et al.; "Absolute bioavailability of testosterone after oral administration of testosterone-undecanoate and testosterone"; European Journal of Drug Metabolism and Pharmacokinetics; (1986); pp. 145-149; vol. 11(2); [Sourcelink] <URL: http://www.ncbi.nim.nih.gov/pubmed/3770015 >; [Abstract].

Temina et al.; "Diversity of the fatty acids of the Nostoc species and their statistical analysis"; Microbiological Research; (2007); pp. 308-321; Elsevier GmbH.

Tenover; "The Androgen-Deficient Aging Male: Current Treatment Options"; Reviews in Urology; (2003); pp. S22-S28; vol. 5, Suppl. 1.

TESTIM® Product Label and Medication Guide; (Sep. 2009); Labeler—A-S Medications Solutions LLC; Revised Jun. 2013; 17 pages.

TORPAC® Inc.; "Capsule Size Chart, Metric Table and English Table"; (2000); 3 pages; Torpac Inc., Fairfield, New Jersey; [Internet] [retrieved on Sep. 2014] [retrieved from <URL: www.torpac.com >].

Treat et al.; "Liposome Encapsulated Doxorubicin preliminary result of Phase I and Phase II Trials"; Liposomes in the Therapy of Infectious Diseases and Cancer; Lopez-Berestein and Fidler (Eds.); (1989); pp. 353-365; Liss, New York.

Tso, et al; "Intestinal Absorption and Lymphatic Transport of a High γ-Linolenic Acid Canola Oil in Lymph Fistula Sprague-Dawley Rats"; The Journal of Nutrition; (2002); pp. 218-221; American Society for Nutritional Sciences.

Wang, et al.; "Long-term testosterone gel (AndroGel®) Treatment Maintains Beneficial Effects on Sexual Function and Mood, Lean and Fat Mass and Bone Mineral Density in Hypogonadal Men"; Journal of Clinical Endocrinology & Metabolism; (2004); pp. 2085-2098; vol. 89.

Webster et al.; "Validation of Pharmaceutical Potency Determinations by Quantitative Nuclear Magnetic Resonance Spectrometry"; Journal of Applied Spectroscopy; (May 2010); pp. 537-542; vol. 64(5).

Wilson et al.; "The Behaviour of Fats and Oils in the Upper G.I. Tract"; Bulletin Technique Gattefosse; (1997); pp. 13-18; vol. 90.

Winne; "Dependence of Intestinal Absorption in Vivo on the Unstirred Layer"; Archives of Pharmacology; (1978); pp. 175-181; vol. 304.

Yassin et al.; "Long-acting testosterone undecanoate for parenteral testosterone therapy"; Therapy, Future Drugs; (2006); pp. 709-721; vol. 3(6).

Yin et al., "Dietary Fat Modulates the Testosterone Pharmacokinetics of a New Self-Emulsifying Formulation of Oral Testosterone Undecanoate in Hypogonadal Men"; Journal of Andrology; (Nov./Dec. 2012); pp. 1282-1290; vol. 33(6).

Yin et al.; "Reexamination of Pharmacokinetics of Oral Testosterone Undecanoate in Hypogonadal Men with a New Self-Emulsifying Formulation"; Journal of Andrology; (2012); pp. 190-201; vol. 33(2).

Zhi et al.;"Effects of dietary fat on drug absorption"; Clinical Pharmacology & Therapeutics; (Nov. 1995); pp. 487-491; vol. 58(5).

International search report issued Mar. 1, 2018, in International Application No. PCT/US17/63535, filed Nov. 28, 2017; 2 pages.

Supplementary European Search Report dated Jul. 3, 2020, in EP Application No. 17874365.4, filed Nov. 28, 2017; 12 pages.

* cited by examiner

ORAL TESTOSTERONE UNDECANOATE THERAPY

PRIORITY DATA

This application claims the benefit of U.S. Provisional Application Ser. No. 62/427,103, filed on Nov. 28, 2016, U.S. Provisional Application Ser. No. 62/428,336, filed on Nov. 30, 2016, and U.S. Provisional Application Ser. No. 62/442,612, filed on Jan. 5, 2017, each of which is incorporated herein by reference.

BACKGROUND

Most testosterone based pharmaceutical products on the market employ dose titration schemes to ensure that patients are safely (e.g., avoiding unacceptably high testosterone levels) and efficaciously treated (e.g., achieving typical eugonadal testosterone levels in hypogonadal patients). Dose titrations are typically required because different patients can absorb and metabolize testosterone based products in substantially different manners. A dose of a testosterone product for one patient that provides safe and efficacious testosterone levels may not provide safe and efficacious levels for another patient.

SUMMARY OF INVENTION

Disclosed herein is an oral testosterone therapy ("TT") dosing regimen. In a specific aspect, the TT involves oral administration of a fixed daily dose of a testosterone ester. For example, where the testosterone ester is testosterone undecanoate (TU), a fixed dose within the range of 420-500 mg per day of oral TU is unexpectedly and particularly efficacious and safe for testosterone replacement therapy. In another example where the testosterone ester is TU, the fixed daily dose can be provided as 210-250 mg of oral TU twice per day for a total daily dose of 420-500 mg TU. Surprisingly, these fixed dose regimens require no dose titration to provide safe and efficacious serum testosterone levels to a substantial proportion of subjects (e.g., those needing testosterone replacement therapy). Thus, in some aspects, the fixed dose is provided as an oral pharmaceutical composition comprising a testosterone ester (e.g., testosterone undecanoate) and a pharmaceutically acceptable carrier, for once daily, or twice daily, etc. administration, with a meal, to a subject (e.g., a male having a condition associated with a deficiency or absence of endogenous testosterone). In some implementations, the daily dose is administered three times per day e.g., a 450 mg daily dose of testosterone undecanoate is administered as 150 mg three times a day or a 474 mg daily dose is administered as 158 mg three times a day.

In some embodiments, specific measures can be used to determine whether or not the therapy should continue or be discontinued. For example, biomarkers such as consistency of unacceptable testosterone (T) levels from a safety or efficacy standpoint, whether hematocrit levels rise above a threshold value, whether Prostate Specific Antigen ("PSA") levels rise above a threshold value, or any other appropriate measure or marker can be used to determine whether or not the therapy should be discontinued.

DETAILED DESCRIPTION OF INVENTION

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth.

It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an," and "the" include plural referents unless the context clearly dictates otherwise. Thus, for example, reference to "polymer" can include a plurality of such polymers.

As used herein, "AUC" refers to the area under the serum concentration-time curve As used herein, "AUCt" refers to the area under the serum concentration-time curve from time zero to time of last measurable concentration.

As used herein, "$C_{avg}$" refers to average serum concentration over 24 hours.

As used herein, "$C_{max}$" refers to maximum observed serum concentration per dose over dosing interval (or daily).

As used herein, "$T_{max}$" refers to the time to maximum observed serum concentration.

As used herein, "TT" refers to testosterone therapy. In a specific definition, TT means any condition wherein serum testosterone is below the normal eugonadal range, such as 300 ng/dL when measured on two separate occasions in the morning. In another definition, the TT described herein can be used to treat patients that are eugonadal (or hypogonadal) for a condition other than specifically having testosterone levels lower than 300 ng/dL. In another specific definition, TT refers to testosterone replacement therapy e.g., to treat a condition associated with a deficiency or absence of endogenous testosterone.

As used herein, "T equivalent dose" from a TU dose is a testosterone equivalent dose that can be released from the bioreversible TU ester. For example, 158 mg of TU is equivalent to 100 mg of T.

As used herein, "Eugonadal range" is the typical range of serum testosterone found in patients not needing TT, normal eugonadal range, is defined as the range with an average testosterone lower limit of ~300 ng/dL and average testosterone upper limit of 1000 ng/dL. It is understood that this normal range could vary depending on the testosterone assay utilized and variability among labs due to specific assay used by individual lab and patient demographics. Therefore, the lower limit of normal eugonadal range could also be 250 ng/dL. Similarly, the upper limit of normal eugonadal range could be 1040 or 1100, or 1500 ng/dL.

As used herein, "dosing regimen" or "administration regimen" can be used interchangeably and refer to specific dosing and administration of a TU containing product. In a specific embodiment, the dosing regimen typically entails daily dose, number of pills per dose, number of doses per day, and whether or not to take with food or fasting. The dosing regimen can also provide relevant instructions regarding the above, for healthcare providers and patients, in some embodiments. Some products (but not the product described herein) involve dose titration or a dose adjustment scheme, in patients needing adjustment, based on a patient's response to the product assessed via measured T measured T levels post dosing at steady state. A practical dosing regimen is the one that is easy to comprehend for implementation. The dosing regimen of this invention is a fixed dose dosing regimen for TT that does not need dose titration.

As used herein, "fixed dose" refers to the same (e.g. unchanging) daily dose of testosterone undecanoate being used for a given patient throughout a therapy regimen with no dose changes. "Single," "singular" or "unitary" fixed dose means that the fixed dose is administered only once daily (e.g., one dose of 450 mg TU per day, one dose of 474 mg TU per day, etc., for example), which can be administered via one or more unit dosage forms during a common administration event or at a common administration time point. "No titration needed" (or "without titration") means that, for a given patient, a fixed dose can provide suitable TT without the need to titrate the testosterone dosage for the patient. In some examples, "no titration needed" or "without titration" can mean that the fixed dose is not adjusted throughout the TT.

As used herein, "Discontinuation of TT" means the dosing regimen for the patient is unsuitable for TT and should be temporarily stopped until relevant markers (e.g., biomarkers, T levels, or any other suitable marker) improve or alternatively, it may be deemed that it is permanently unsuitable for TT in the patient. As used herein, "Consistently" refers to at least two or more times or occurrences as measured on two separate occasions with a least a gap of 24 hours preferably in the morning.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, "subject" or "patient" are used interchangeably and refer to a mammal that may benefit from the administration of a composition described herein. In one aspect the mammal may be a human.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid and/or liquid (i.e. solution). Furthermore, the term "dosage form" can include one or more formulation(s) or composition(s) provided in a form suitable for administration to a subject.

As used herein, "effective amount" refers to an amount of an ingredient which, when included in a composition, is sufficient to achieve an intended compositional or physiological effect. Thus, a "therapeutically effective amount" refers to a substantially non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Additionally, in some cases an "effective amount" or a "therapeutically effective amount" may not be achieved in a single dose. Rather, in some examples, an "effective amount" or a "therapeutically effective amount" can be achieved after administering a plurality of doses over a period of time, such as in a pre-designated dosing regimen. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical and nutritional sciences as well as medicine.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 mg to about 80 mg" should also be understood to provide support for the range of "50 mg to 80 mg." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-2, from 1-3, from 1-4, from 2-3, from 2-4, from 2-5, from 3-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

It is noted that testosterone levels can be monitored via a variety of testosterone assays. Such testosterone assays (e.g., for serum testosterone, total testosterone, free testosterone etc.) can be performed as part of a diagnosis of hypogonadism, a treatment efficacy assessment, or discontinuation of therapy. The assays themselves can be radioimmunoassays via commercial kits, validated mass spectrometric methods, or any other suitable assay.

It is also noted that typical regulatory approval targets for TT are based on responder outcomes targeted for patients on TT such that average daily T levels ($C_{avg}$) are restored in the normal eugonadal range in at least 75% of the treated patients and no more than 15% of the patients experience maximum serum T concentrations ($C_{max}$)>1500 ng/dL. Unacceptably high serum T level is typically defined as maximum serum concentrations of >1800 ng/dL observed in a patient post dosing in the dosing interval (or daily interval) is typically assessed by a percentage of patients in a group that shows $C_{max}$>1800 ng/dL.

Described herein, in one embodiment, is a method of restoring testosterone levels in a patient needing testosterone therapy (TT). The method can include administering a therapeutically effective amount of a testosterone ester, such as testosterone undecanoate (TU), to the patient via an oral dosage form. The oral dosage form can be administered to the patient in a fixed dose dosing regimen. It is noted that for the sake of clarity and brevity, TU is generally referred to in this disclosure as an example testosterone ester. These references to TU are not intended to be particularly limiting unless otherwise specified. More broadly, references to TU can generally refer to any suitable testosterone ester.

Described herein, in one embodiment, is a method of restoring a dihydrotestosterone (DHT) to testosterone (T) ratio (DHT/T) to a normal range (e.g. 0.05-0.33) in patients needing TT. The method can include administering a therapeutically effective amount of a testosterone ester, such as TU, to a patient via an oral dosage form using a fixed dose dosing regimen. In one aspect, the fixed dose dosing regimen can include a single daily dose of a therapeutically effective amount of TU to an individual in need of treatment. In another aspect, the fixed dose dosing regimen can include oral administration of a therapeutically effective amount of TU twice per day. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three time per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method that can provide safe and effective testosterone therapy in patients needing TT with a TU-containing oral dosage form using a fixed dose dosing regimen. In one aspect, the method comprises oral administration of therapeutically effective amount of TU to a patient in need of treatment via a single fixed dose dosing regimen. In one aspect, the method comprises oral administration of TU twice per day in a fixed dose dosing regimen. In one aspect, the method comprises oral administration of a therapeutically effective amount of TU twice per day with food. In one aspect, the method comprises oral administration of a therapeutically effective amount of TU twice per day with fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen of TU which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring average testosterone levels to a normal eugonadal range in patients needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen. In one aspect, the method comprises oral administration of a therapeutically effective amount of TU twice per day in a fixed dose dosing regimen of TU. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen of TU which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring average testosterone levels to a normal eugonadal range while avoiding unacceptably high serum testosterone levels in patients needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen of TU which provides from about 215 mg to 245 mg of TU administered twice daily. In one aspect, the method comprises oral administration of TU in a single fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring average testosterone levels to a normal eugonadal range while avoiding unacceptably high testosterone levels (e.g. maximum testosterone concentration post administration >1500 ng/dL) in patients needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing. In one aspect, the method comprises oral administration of a therapeutically effective amount of TU in a fixed dose dosing regimen of TU twice a day. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

In one aspect of these embodiments, ≤20% of the treated patients (e.g., in a population of patients or subjects where the population is 10 or more, 20 or more, 30 or more, 40 or more, 50 or more, 60 or more, 70 or more, 80 or more, 90 or more, or 100 or more patients or subjects) have unacceptably high testosterone levels (e.g., maximum serum testosterone concentration post administration >1500 ng/dL) when treated with an oral dosage form including a therapeutically effective amount of TU via a fixed dose dosing regimen that does not need dose adjustment or titration and that provides ≤520 mg of TU per day. In one aspect, the method comprises oral administration of a therapeutically effective amount of TU to a patient in need of treatment via a fixed dose dosing regimen. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen of TU which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

In one aspect of these embodiments, ≤15% of the treated patients (e.g., in a population of patients or subjects where the population is 10 or more, 20 or more, 30 or more, 40 or more, 50 or more, 60 or more, 70 or more, 80 or more, 90 or more, or 100 or more patients or subjects) experience maximum testosterone concentration post administration >1500 ng/dL when treated with an oral dosage form including a therapeutically effective amount of TU to a patient via a fixed dose dosing regimen that does not need dose adjustment or titration and that provides ≤480 mg daily dose of TU. In one aspect, the method comprises oral administration of a therapeutically effective amount of TU to a patient in need of treatment via a fixed dose dosing regimen. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 480 mg of TU per day. In one aspect, the method comprises oral administration of TU in a single fixed dose dosing regimen which provides from about 430 mg to 480 mg of TU per day. In one aspect, the method comprises oral administration of TU in a fixed dose dosing regimen which provides from about 210 mg to 240 mg of TU administered twice daily. In one aspect, the method comprises oral administration of TU in a fixed dose dosing regimen which provides from about 215 mg to 240 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels to a normal eugonadal range while avoiding unacceptably high testosterone levels (e.g., maximum serum testosterone concentration post administration >1800 ng/dL) in ≥90% of patients (e.g., in a population of patients or subjects where the population is 10 or more, 20 or more, 30 or more, 40 or more, 50 or more, 60 or more, 70 or more, 80 or more, 90 or more, or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels to a normal eugonadal range while avoiding unacceptably high serum testosterone levels, (e.g., maximum serum testosterone concentration post administration >1800 ng/dL) in ≥95% patients (e.g., in a population of patients or subjects where the population is 10 or more, 20 or more, 30 or more, 40 or more, 50 or more, 60 or more, 70 or more, 80 or more, 90 or more, or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels to a normal eugonadal range while avoiding unacceptably high serum testosterone levels (e.g., maximum serum testosterone concentration post administration >2500 ng/dL) in patients needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen of TU. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels to a normal eugonadal range while avoiding unacceptably high serum testosterone levels (e.g., maximum serum testosterone concentration post administration >2500 ng/dl) in ≥98% patients (e.g., in a population of patients or subjects where the population is 10 or more, 20 or more, 30 or more, 40 or more, 50 or more, 60 or more, 70 or more, 80 or more, 90 or more, or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a single fixed dose dosing regimen of TU. In one aspect, the method comprises oral administration of a therapeutically effective amount of TU twice per day in a fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels to a normal eugonadal range while avoiding unacceptably high serum testosterone levels (e.g., maximum serum testosterone concentration post administration >2500 ng/dl) in all patients (e.g., in a population of patients or subjects where the population is 10 or more, 20 or more, 30 or more, 40 or more, 50 or more, 60 or more, 70 or more, 80 or more, 90 or more, or 100 or more patients or subjects) needing TT. The method can include administering a therapeutically effective amount of a testosterone ester to a patient via an oral dosage form using a fixed dose dosing regimen. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels in a patient needing TT with an oral dosage form administered in a dosing regimen that does not need dose adjustment or titration and that provides at least 430 mg of TU per day. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 430 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 215 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 430 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 440 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 440 mg to 500 mg of TU per day. In one aspect, the method comprises oral administration of TU in a single fixed dose dosing regimen which provides from about 440 mg to 490 mg of TU per day. In one aspect, the method comprises oral administration of TU in a fixed dose dosing regimen which provides from about 220 mg to 250 mg of TU administered twice daily. In one aspect, the method comprises oral administration of TU in a fixed dose dosing regimen which provides from about 220 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 450 mg of TU per day and wherein at least 75% of the patients (e.g., in a population of patients or subjects where the populations is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 450 mg to 500 mg of TU per day. In one aspect, the method comprises oral administration of TU in a single fixed dose dosing regimen which provides from about 450 mg to 490 mg of TU per day. In one aspect, the method comprises oral administration of TU in a fixed dose dosing regimen which provides from about 225 mg to 250 mg of TU administered twice daily. In one aspect, the method comprises oral administration of TU in a fixed dose dosing regimen which provides from about 225 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 460 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 460 mg to 500 mg of TU per day. In one aspect, the method comprises oral administration of TU in a single fixed dose dosing regimen which provides from about 460 mg to 490 mg of TU per day. In one aspect, the method comprises oral administration of TU in a fixed dose dosing regimen which provides from about 230 mg to 250 mg of TU administered twice daily. In one aspect, the method comprises oral administration of TU in a fixed dose dosing regimen which provides from about 230 mg to 245 mg of TU administered twice daily. In one aspect, the method comprises oral administration of TU in a fixed dose dosing regimen which provides about 230 mg TU administered twice daily (e.g., about 460 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 460 mg daily dose of testosterone undecanoate is administered as 153.3 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 470 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 435 mg to 500 mg of TU per day. In one aspect, the method comprises oral administration of TU in a single fixed dose dosing regimen which provides from about 435 mg to 490 mg of TU per day. In one aspect, the method comprises oral administration of TU in a fixed dose dosing regimen which provides from about 235 mg to 250 mg of TU administered twice daily. In one aspect, the method comprises oral administration of TU in a fixed dose dosing regimen which provides from about 235 mg to 245 mg of TU administered twice daily. In one aspect, the method comprises oral administration of TU in a fixed dose dosing regimen which provides about 235 mg TU administered twice daily (e.g., about 470 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 474 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 474 mg to 500 mg of TU per day. In one aspect, the method comprises oral administration of TU in a single fixed dose dosing regimen which provides from about 474 mg to 490 mg of TU per day. In one aspect, the method comprises oral administration of TU in a fixed dose dosing regimen which provides from about 237 mg to 250 mg of TU administered twice daily. In one aspect, the method comprises oral administration of TU in a fixed dose dosing regimen which provides from about 237 mg to 245 mg of TU administered twice daily. In one aspect, the method comprises oral administration of TU in a fixed dose dosing regimen which provides about 237 mg TU administered twice daily (e.g., about 474 mg TU total daily dose). In one aspect, the method comprises oral administration of TU in a fixed dose dosing regimen which provides about 240 mg TU administered twice daily (e.g., about 480 mg TU total daily dose). In some implementations, the daily dose is administered three times per day e.g., a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 480 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 480 mg to 500 mg of TU per day. In one aspect, the method comprises oral administration of TU in a single fixed dose dosing regimen which provides from about 480 mg to 490 mg of TU per day. In one aspect, the method comprises oral administration of TU in a fixed dose dosing regimen which provides from about 240 mg to 250 mg of TU administered twice daily. In one aspect, the method comprises oral administration of TU in a fixed dose dosing regimen which provides from about 245 mg to 250 mg of TU administered twice daily. In one aspect, the method comprises oral administration of TU in a fixed dose dosing regimen which provides about 240 mg TU administered twice daily (e.g., about 480 mg TU total daily dose). In one aspect, the method comprises oral administration of TU in a fixed dose dosing regimen which provides about 245 mg TU administered twice daily (e.g., about 490 mg TU total daily dose). In some implementations, the daily dose is administered three times per day e.g., a 486 mg daily dose is administered as 162 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 440 mg of TU per day and wherein at least 80% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 440 mg to 500 mg of TU per day. In one aspect, the method comprises oral administration of TU in a single fixed dose dosing regimen which provides from about 440 mg to 490 mg of TU per day. In one aspect, the method comprises oral administration of TU in a fixed dose dosing regimen which provides from about 220 mg to 250 mg of TU administered twice daily. In one aspect, the method comprises oral administration of TU in a fixed dose dosing regimen which provides from about 220 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 460 mg of TU per day and wherein at least 85% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 460 mg to 500 mg of TU per day. In one aspect, the method comprises oral administration of TU in a single fixed dose dosing regimen which provides from about 460 mg to 490 mg of TU per day. In one aspect, the method comprises oral administration of TU in a fixed dose dosing regimen which provides from about 230 mg to 250 mg of TU administered twice daily. In one aspect, the method comprises oral administration of TU in a fixed dose dosing regimen which provides from about 230 mg to 245 mg of TU administered twice daily. In one aspect, the method comprises oral administration of TU in a fixed dose dosing regimen which provides about 230 mg TU administered twice daily (e.g., about 460 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 474 mg daily dose is administered as 158 mg three times a day. In other implementations, a subject can change from twice daily dosing to three times a day dosing or vice-versa.

Described herein, in one embodiment, is a method of restoring $C_{avg}$ testosterone levels to a normal range by administering TU in an oral dosage form using a dosing regimen that does not need dose adjustment or titration and that provides at least 490 mg of TU per day and wherein at least 90% of the patients (e.g., in a population of patients or subjects where the population is 10 or more, 20 or more, 30 or more, 40 or more, 50 or more, 60 or more, 70 or more, 80 or more, 90 or more, or 100 or more patients or subjects) treated using the dosing regimen described herein achieve $C_{avg}$ testosterone levels within the normal range. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 490 mg to 500 mg of TU per day. In one aspect, the method comprises oral administration of TU in a single fixed dose dosing regimen which provides from about 495 mg to 500 mg of TU per day. In one aspect, the method comprises oral administration of TU in a fixed dose dosing regimen which provides from about 245 mg to 250 mg of TU administered twice daily. In one aspect, the method comprises oral administration of TU in a fixed dose dosing regimen which provides from about 247 mg to 500 mg of TU administered twice daily. In one aspect, the method comprises oral administration of TU in a fixed dose dosing regimen which provides about 245 mg TU administered twice daily (e.g., about 490 mg TU total daily dose). In one aspect, the method comprises oral administration of TU in a fixed dose dosing regimen which provides about 247 mg TU administered twice daily (e.g., about 494 mg TU total daily dose). In some implementations, the daily dose is administered three times per day. In other implementations, a subject can change from twice daily dosing to three times a day dosing or vice-versa.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of from 430 mg to 480 mg. In one aspect, the method comprises oral administration of a therapeutically effective amount of TU to a patient in need of treatment via a fixed dose dosing regimen. In one aspect, the method comprises oral administration of a therapeutically effective amount of TU twice per day in a single fixed dose dosing regimen. In one aspect, the method comprises oral administration of a therapeutically effective amount of TU twice per day with food or fat containing food. In one aspect, the method comprises oral administration of TU in a single fixed dose dosing regimen which provides from about 420 mg to 500 mg of TU per day. In one aspect, the method comprises oral administration of TU in a single fixed dose dosing regimen which provides from about 430 mg to 490 mg of TU per day. In one aspect, the method comprises oral administration of TU in a fixed dose dosing regimen which provides from about 210 mg to 250 mg of TU administered twice daily. In one aspect, the method comprises oral administration of TU in a fixed dose dosing regimen which provides from about 215 mg to 245 mg of TU administered twice daily. In one aspect, the method comprises oral administration of TU in a fixed dose dosing regimen which provides about 225 mg TU administered twice daily (e.g., about 450 mg TU total daily dose). In one aspect, the method comprises oral administration of TU in a fixed dose dosing regimen which provides about 237 mg TU administered twice daily (e.g., about 474 mg TU total daily dose). In some implementations, the daily dose is administered three times per day e.g., a 450 mg daily dose of testosterone undecanoate is administered as 150 mg three times a day or a 474 mg daily dose is administered as 158 mg three times a day. In other implementations, a subject can change from twice daily dosing to three times a day dosing or vice-versa.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 480 mg.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 474 mg.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 460 mg.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 450 mg.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 440 mg.

Described herein, in one embodiment, is a method of restoring testosterone levels in a patient needing TT to within normal T levels while avoiding unacceptably high T levels. The method can include administering TU via an oral dosage form using a dosing regimen that does not need a dose adjustment or titration and that provides a daily amount of TU of about 430 mg.

In one embodiment, an unexpected finding of these studies, as outlined in the Examples and described herein, is the surprising discovery that a TT dosing regimen including an appropriate single fixed oral dose of TU in the range from 430 mg to 500 mg (or 430-480 mg) can obviate the need for a titration scheme or dose adjustment. This is unexpected since recent previous attempts to obtain regulatory approval of an oral TU based TT were based on dose titration schemes which were thought to be needed to ensure adequate efficacy and safety of the therapy. Additionally, many marketed TTs require dose titrations or adjustment as indicated on the product's label.

While any oral dosage form can be utilized in the dosing regimen of this invention for TT, in some examples the dosage form can be a capsule comprised of pharmaceutically acceptable components. In one embodiment, the dose of TU is 200-250 mg (e.g., 2 capsules of 100-125 mg TU or one capsule having about 200-250 mg TU) administered orally two times daily for a total daily dose of TU from 400-500 mg (T equivalent dose of approximately 250-316 mg/day). The oral dosage form can be administered with food (e.g., co-administered) having at least 10 g of fat, at least 15 g of fat, at least 20 g of fat, or at least 30 g of fat, or an amount of fat within the range of 10-60 g.

The dosing regimen of this invention can include a daily dose of TU administered as a four times per day (QID), a thrice per day (TID), a twice per day (BID), or a once per day (QD) dosage. Whatever the number of daily doses, each dose can be equally divided to provide a total daily dose of TU between 400-500 mg.

In one embodiment, the dose of testosterone undecanoate is 215-245 mg of testosterone undecanoate (e.g., 2 capsules of 107.5-122.5 mg) administered orally two times daily for a total daily dose of 430-490 mg.

Thus, in one embodiment, the dose of testosterone undecanoate can be 225 mg of testosterone undecanoate (e.g., one capsule of 225 mg, two capsules of 112.5 mg or three capsules of 75 mg) administered orally two times daily for a total daily dose of 450 mg.

In yet another embodiment, the dose of testosterone undecanoate can be about 237 mg of testosterone undecanoate (e.g., one capsule of 237 mg TU or e.g., two capsules adding up to 237 mg) administered orally two times daily for a total daily dose of 474 mg.

In some implementations of the methods and regimens described herein, a subject or patient can change from a twice daily regimen to a three times a day regimen or vice-versa.

The oral testosterone replacement therapy described herein was discovered to be safe and efficacious. For example, it is believed that the TT described herein meets (1), (2), (3), (4), and/or (5) of the following criteria when used in a sufficient population of individuals needing such therapy (e.g., hypogonadal men):

(1) Proportion of subjects with average serum T ($C_{avg}$) within the normal range
(e.g., 300-1000 ng/dL): ≥75%, 77%, 79%, 81%, 83%, 85%, 86%, 87%, 88%, 89%, 90%, 91%, 92%, 93%, 94% or 95% or more;

(2) Proportion of subjects with average serum T ($C_{avg}$) within the normal range: ≥65%,
67%, 69%, 71%, 73%, 75%, 76%, 77%, 78%, 79%, 80%, 81%, 82%, 83%, 84% or 85% or more with a lower bound 95% CI (Confidence Interval);

Proportion with maximum serum T ($C_{max}$) outside the normal range:
(3) $C_{max}$>1500 ng/dL (no greater than 15%, 16%, 17%, 18%, 19% 20%, 21%, 22%, 23%, 24% or 25%);
(4) $C_{max}$ between 1800 and 2499 ng/dL (no greater than 5% 6%, 7%, 8%, 9% or 10%); and
(5) $C_{max}$≥2500 ng/dL (0%, or no greater than 1%, 2%, 3%, 4% or 5%).

In this context, a population of individuals typically refers to at least 20 individuals (e.g., in need of treatment like hypogonadal males) and preferable at least 25, 30, 35, 40, 45, 50, 55, 60, 65, 70, 75, 80, 85, 90, 95 or 100 individuals or more.

In some embodiments, testosterone concentrations (e.g., blood, serum, or plasma) can be checked periodically, e.g., 3-8 hours after the morning dose, starting as soon as one month or two weeks (or sooner) after initiating treatment with testosterone undecanoate. When the total testosterone concentration consistently exceeds 1200, 1300, 1400, 1500, 1600, 1700, 1800, 1900, 2000, 2100, 2200, 2300, 2400 or 2500 ng/dL, therapy with testosterone undecanoate can be discontinued as advised by trained medical personnel (or in another alternative, the patient can switch to a three times a day regimen e.g., 450 mg daily dose can be switched from 225 mg twice a day to 150 mg three times a day). If the total testosterone concentration is consistently below 300 ng/dL, an alternative treatment can be considered as advised by trained medical personnel. As used in this paragraph, consistently can refer to two or more times or occurrences.

In another embodiment, testosterone (e.g., blood, serum, or plasma) concentrations can be checked periodically, e.g., any time between 3-8 hours after the morning dose, starting as soon as one month after initiating treatment with testosterone undecanoate. If the total testosterone concentration consistently exceeds 2500 ng/dL, therapy with testosterone undecanoate can be discontinued as advised by trained medical personnel (or in another alternative, the patient can switch to a three times a day regimen e.g., 450 mg daily dose can be switched from 225 mg twice a day to 150 mg three times a day or a 474 mg daily dose at 237 mg twice a day can be switched to 158 mg three times a day). If the total testosterone concentration is consistently below 300 ng/dL, an alternative treatment can be considered as advised by trained medical personnel. As used in this paragraph, consistently can refer to two or more times or occurrences.

In yet another embodiment, increases in hematocrit levels, reflective of increases in red blood cell mass, may require discontinuation of oral testosterone undecanoate. Hematocrit levels can be checked prior to initiating treatment. In some examples, it can be appropriate to re-evaluate the hematocrit levels starting from 3 months after starting treatment, and then annually. In some cases, if hematocrit levels become elevated, the therapy can be discontinued until hematocrit levels decrease to an acceptable level.

Thus, in one embodiment, the dosing regimen comprises orally administering a dosage form that comprises TU and a carrier including a pharmaceutically acceptable additive. The pharmaceutically acceptable additives of this invention can include one or more lipophilic additives, one or more hydrophilic additives, other suitable pharmaceutically acceptable additives, or a combination thereof.

Thus, in some embodiments, orally administered testosterone undecanoate compositions can be used in the following exemplary replacement therapies described below or previously in this specification.

In one example, a testosterone replacement therapy for a male patient having a condition associated with a deficiency or absence of endogenous testosterone can include orally administering a fixed dose of a therapeutically effective amount of testosterone undecanoate to the patient with food.

In some examples, the fixed dose is 145-165 mg testosterone undecanoate per dose.

In some examples, the fixed dose is about 150 mg testosterone undecanoate per dose.

In some examples, the fixed dose is about 158 mg testosterone undecanoate per dose.

In some examples, the fixed dose can be from 200 mg to 250 mg TU.

In some examples, the fixed dose is 220-230 mg testosterone undecanoate per dose.

In some examples, the fixed dose is 400-500 mg testosterone undecanoate per day.

In some examples, the fixed dose is 230-240 mg testosterone undecanoate per dose.

In some examples, the fixed dose is 235-239 mg testosterone undecanoate per dose.

In some examples, the fixed dose is 223-227 mg testosterone undecanoate per dose.

In some examples, the fixed dose is 465-485 mg testosterone undecanoate per day.

In some examples, the fixed dose is 445-455 mg testosterone undecanoate per day.

In some examples, a serum testosterone level of said male is determined after initiation of therapy.

In some examples, a serum testosterone level of said male is determined after initiation of therapy wherein unacceptably high serum testosterone levels after a fixed dose administration of testosterone undecanoate indicates that the male discontinues said therapy.

In some examples, a serum testosterone level of said male is determined after initiation of therapy wherein unacceptably low serum testosterone levels after a fixed dose administration of testosterone undecanoate indicates that the male discontinues said therapy.

In some examples, the testosterone undecanoate is formulated with a lipophilic surfactant, a hydrophilic surfactant, or both.

In some examples, the testosterone undecanoate is formulated with a triglyceride.

In some examples, the testosterone undecanoate is formulated with a fatty acid, a monoglyceride, a diglyceride, a triglyceride, a hydrophilic surfactant, a solidifying agent, or a combination thereof.

In some examples, the fixed dose is about 237 mg testosterone undecanoate per dose.

In some examples, the fixed dose is about 225 mg testosterone undecanoate per dose.

In some examples, the fixed dose is about 474 mg testosterone undecanoate per day.

In some examples, the fixed dose is about 450 mg testosterone undecanoate per day.

In some examples, when the total serum testosterone concentration consistently exceeds 1200, 1300, 1400, 1500, 1600, 1700, 1800, 1900, 2000, 2100, 2200, 2300, 2400 or 2500 ng/dL, therapy with testosterone undecanoate is discontinued.

In some examples, when the total serum testosterone concentration consistently exceeds 2500 ng/dL, therapy with testosterone undecanoate is discontinued.

In some examples, when the total serum testosterone concentration consistently exceeds 2100 ng/dL, therapy with testosterone undecanoate is discontinued.

In some examples, when the total serum testosterone concentration consistently exceeds 1800 ng/dL, therapy with testosterone undecanoate is discontinued.

In some examples, when the total serum testosterone concentration consistently exceeds 1500 ng/dL, therapy with testosterone undecanoate is discontinued.

In some examples, when the total serum testosterone concentration is consistently below 300 ng/dL, therapy with testosterone undecanoate is discontinued.

In some examples, discontinuation criteria are assessed at steady state.

In some examples, discontinuation criteria are assessed at steady state by measuring serum testosterone concentrations.

In some examples, discontinuation criteria are assessed at steady state by measuring serum testosterone concentrations 1 to 12 hours after a fixed dose administration of the oral testosterone undecanoate.

In some examples, the therapy is discontinued when the subject's hematocrit or PSA levels are unacceptably high.

In some examples, the therapy meets 1, 2, 3, 4, or 5 of the following criteria when used in a sufficient population of individuals needing such therapy:

(1) Proportion of subjects with average serum T ($C_{avg}$) within the normal range (300-1000 ng/dL): ≥75%, 77%, 79%, 81%, 83%, 85%, 86%, 87%, 88%, 89%, 90%, 91%, 92%, 93%, 94% or 95% or more;

(2) Proportion of subjects with average serum T ($C_{avg}$) within the normal range: ≥65%, 67%, 69%, 71%, 73%, 75%, 76%, 77%, 78%, 79%, 80%, 81%, 82%, 83%, 84% or 85% or more with a lower bound 95% CI (Confidence Interval);

Proportion with maximum serum T ($C_{max}$) outside the normal range:

(3) $C_{max}$>1500 ng/dL (not >15%, 16%, 17%, 18%, 19% or 20%);

(4) $C_{max}$ between 1800 and 2499 ng/dL (not >5% 6%, 7%, 8%, 9% or 10%);

(5) $C_{max}$≥2500 ng/dL (none or not >1%, 2%, 3%, 4% or 5%);

wherein a population of individuals refers to typically at least 20 individuals or at least 25, 30, 35, 40, 45, 50, 55, 60, 65, 70, 75, 80, 85, 90, 95 or 100 individuals or more.

Thus, the testosterone replacement therapy described herein, when used with a population of male subjects, provides safe and efficacious testosterone replacement therapy.

Examples of TU Compositions and Dosage Forms

The dosing regimens involving TU compositions and dosage forms are exemplified below for oral TT. The compositions and dosage forms described herein can be used with oral testosterone products and particularly TU that are suitable for oral administration. Any suitable oral unit dosage form can be used. For example, in some embodiments, the unit dosage form is a hard gelatin or soft gelatin capsule. In other embodiments, the unit dosage form is a tablet or caplet. Other suitable unit dosage forms include, but are not limited to, powder, granulate, particulate, bead, pellet, sprinkle, suspension, solution, tablet, capsule, or combinations thereof. The dosing schemes or regimens described herein can be used with oral testosterone products formulated in any suitable manner.

Some typical pharmaceutical compositions for use herein are provided below.

| Composition 1 | | |
|---|---|---|
| Ingredient Name | Composition 1 % w/w | mg/unit* |
| Testosterone Undecanoate | 10-35 | 100-250 |
| Pharmaceutically Acceptable Carriers | 65-90 | 450-750 |
| Total | 100.0 | 700-850 |

*The unit quantity of each ingredient of the composition can be proportionally adjusted to the quantity for any size or form of unit dosage form such as a capsule or a tablet.

| Composition 2 | | |
|---|---|---|
| Ingredient Name | | Composition 2 % w/w |
| Testosterone Undecanoate | | 10-35 |
| Pharmaceutical Acceptable Carriers | Lipophilic Additives* | 50-90 |
| | Other Additives | 0-40 |
| Total | | 100.0 |

*Preferred Lipophilic Additive include one or more of mono-di glycerides, vegetable oils, fatty acid, triglycerides, phytosterols, Vitamin E, lecithin, omega 3 fatty acids.

| Composition 3 | | |
|---|---|---|
| Ingredient Name | | Composition 3 % w/w |
| Testosterone Undecanoate | | 10-35 |
| Pharmaceutical Acceptable Carriers | Hydrophilic Additives* | 0-40 |
| | Other Additives | 50-90 |
| Total | | 100.0 |

*Preferred Hydrophilic Additives include one or more of Cremophor RH 40, Cremophor EL, Vitamin E, TPGS, Tween 80, labrasol, etc.

| Composition 4 | | |
|---|---|---|
| Ingredient Name | | Composition 4 % w/w |
| Testosterone Undecanoate | | 10-35 |
| Pharmaceutical Acceptable Carriers | Lipophilic Additives | 50-90 |
| | Hydrophilic Additives | 0-40 |
| | Other Additives | 0-20 |
| Total | | 100.0 |

The compositions and dosage forms (e.g. capsule or tablet) described herein can include a variety of pharmaceutically acceptable carriers known in the art. Non-limited examples of the pharmaceutical acceptable carriers include lipophilic additives, hydrophilic additives, other additives, or combinations thereof.

In one embodiment, the lipophilic additives include, but are not limited to, lipidic solubilizers, lipophilic surfactants, or combinations thereof. In some embodiments, the lipidic solubilizers can comprise at least about 50 wt % of the pharmaceutically acceptable carrier. Non-limiting examples of lipidic solubilizers can include triglycerides, tocopherol, tocopherol derivatives, fatty acids, fatty acid glycerides, or combinations thereof. The triglycerides can include hydrogenated soyabean oil, hydrogenated vegetable oil, corn oil, olive oil, soyabean oil, peanut oil, sesame oil, or combinations thereof. In another embodiment, the fatty acids can include caprylic acid, capric acid, lauric acid, myristic acid, palmitic acid, stearic acid, ricinoleic acid, arachidic acid, behenic acid, lignoceric acid, cerotic acid, myristoleic acid, palmitoleic acid, sapienic acid, oleic acid, elaidic acid, vaccenic acid, linoleic acid, γ-linoleic acid, linoeladic acid, arachidonic acid, erucic acid, or combinations thereof. In an additional embodiment, the fatty acid glycerides can be monoglycerides, diglycerides, or mixtures thereof. Non-limiting examples of fatty acid glycerides that can be used in the oral pharmaceutical compositions and dosage forms of the present invention include monoglycerides and/or diglycerides derived from sources such as maize oil, poppy seed oil, safflower oil, sunflower oil, borage seed oil, peppermint oil, coconut oil, palm kernel oil, castor oil, or mixtures thereof. In one embodiment, the glyceride derivatives described in the following surfactants may be used as lipidic solubilizers as well.

In one embodiment, a surfactant is considered as a lipophilic surfactant when it has an HLB value of 10 or less. It is important to note that some lipophilic surfactants may also function as the lipidic solubilizer component of the compositions and oral dosage forms. Various lipophilic surfactants can be used including, but not limited to mono- and di-glycerides of fatty acids like glyceryl monolinoleate (e.g. Maisine® 35-1), mono- and di-glycerides of caprylic, capric acid (e.g. Capmul® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. Labrafil® M 2125 CS), PEG-6 almond oil (e.g. Labrafil® M 1966 CS), PEG-6 apricot kernel oil (e.g. Labrafil® M 1944 CS), PEG-6 olive oil (e.g. Labrafil® M 1980 CS), PEG-6 peanut oil (e.g. Labrafil® M 1969 CS), PEG-6 hydrogenated palm kernel oil (e.g. Labrafil®. M 2130 BS), PEG-6 palm kernel oil (e.g. Labrafil® M 2130 CS), PEG-6 triolein (e.g. Labrafil® M 2735 CS), PEG-8 corn oil (e.g. Labrafil® WL 2609 BS), PEG-20 corn glycerides (e.g. Crovol® M40), PEG-20 almond glycerides (e.g. Crovol® A40), lipophilic polyoxyethylene-polyoxypropylene block co-polymers (e.g. Pluronic® L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. Captex® 200), and propylene glycol dioctanoate (e.g. Captex® 800), propylene glycol mono-caprylate (e.g. Capryol® 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. Arlacel® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, cholesterol, sitosterol, phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko), and the like, or mixtures thereof.

In one embodiment, hydrophilic additives are selected from the group consisting of hydrophilic surfactant, celluloses—such as hydroxypropyl celluloses low molecular weight, low viscosity types (e.g., Methocel® E5, E6, E10 E15, LV100 etc. grades) and hydroxypropyl celluloses having higher molecular weight, medium to high viscosity (e.g., Methocel® K4M, K15M, K100M etc); polyvinylpyrrolidones (e.g. Kollidon k17, K30 etc); polyvinyl acetates and combinations thereof.

In further embodiment, a surfactant is considered as a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 hydrogenated castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, lanosterol PEG-24 cholesterol ether (e.g., Solulan C-24, Amerchol), PEG-30 soya sterol (e.g. Nikkol BPS-30, from Nikko), PEG-25 phytosterol (e.g. Nikkol BPSH-25 from Nikko), PEG-30 cholestanol (e.g. Nikkol DHC, from Nikko), or mixtures thereof.

In another aspect, other additives described herein in the oral dosage forms (e.g. powder, granulate, particulate, bead, pellet, sprinkle, suspension, solution, tablet, or capsule) can include binders, bufferants, diluents, disintegrants, flavors, colorants, taste-masking agents, resins, pH modifiers, lubricants, glidants, thickening agent, opacifying agent, humectants, desiccants, effervescing agents, plasticizing agents, antioxidants, solidifying agents, control release agents, the like, or combinations thereof.

For example, a solidifying agent is a pharmaceutically acceptable additive that is in a solid physical state at room temperature. Typically solidifying agents facilitate the solidification of the pharmaceutical compositions of the present invention at temperatures around room temperature. The compositions and capsule fill of the present invention, including those with solidifying agents, can be non-liquid at standard temperature and pressure. In an aspect, the composition and capsule fill can be semi-solid or solid at standard temperature and pressure. When present, the solidifying agent can comprise from about 0.1 wt % to about 20 wt % of the pharmaceutical composition or capsule dosage form. In one embodiment, the solidifying agent can melt at a temperature of about body temperature to about 75° C. Non-limiting examples of solidifying agents include polyethylene glycols; sorbitol; gelatin; stearic acid; cetyl alcohol; cetosterayl alcohol; paraffin wax; polyvinyl alcohol; glyceryl stearates; glyceryl distearate; glyceryl monostearate; glyceryl palmitostearate; glyceryl behenate; waxes; hydrogenated castor oil; hydrogenated vegetable oil; Vit E derivatives, bees wax, microcrystalline wax; sterols; phytosterols; phytosterols fatty acid esters, cholesterol, or mixtures thereof. In one embodiment, the solidifying agent includes a polyethylene glycol (PEG) having molecular weight from about 1000 to about 20,000 and their mixtures. In another embodiment the solidifying agent includes one or more selected from the group consisting of polyethylene glycol; gelatin; stearic acid; polyvinyl alcohol; glyceryl stearates; glyceryl distearate; glyceryl monostearate; glyceryl palmitostearate; hydrogenated castor oil; hydrogenated vegetable oil, cholesterol, and combinations thereof. In an additional embodiment, the solidifying agent includes Vitamin E tocopherol PEG 1000 succinate (D-α-TPGS) or derivatives of D-α-TPGS. In one embodiment, the pharmaceutical composition can be a solid at about room temperature. In yet a further embodiment, a "not dissolved" crystalline testosterone ester can act as a solidifying agent.

The oral compositions of the present invention can be formulated as any suitable dosage form commonly known in the pharmaceutical arts such as granules, tablet, or capsule. In one embodiment the oral pharmaceutical compositions of the present invention can be formulated as oral dosage forms such as capsules or tablets. The capsule size can be any size known in the art and can vary depending on the desired dosage amount. For instance, in one embodiment, the capsule can be a hard gelatin capsule having a fill volume of about 0.25 mL to about 1.1 mL. Similarly, in another embodiment, the capsule can be a soft gelatin capsule having a fill volume of about 0.25 mL to about 1.5 mL.

In a specific embodiment, the compositions of the current invention can be formulated in the form of granules, powder mixtures, or tablets. In a specific embodiment, the testosterone ester present in the dosage form can be present in the form of nanoparticles or amorphous particles, liquid, or mixtures thereof. In another specific embodiment, the testosterone ester present in these dosage form can be present in the form of crystalline, non-crystalline or amorphous particles or a mixtures thereof having an average particle size of about 2000 nm or less, 1500 nm or less, 1000 nm, 800 nm or less, 600 nm or less, 500 nm or less, 400 nm or less, 300 nm or less, 250 nm or less, 200 nm or less, 100 nm or less, 50 nm or less, or 25 nm or less; or the average particle size of said crystalline, non-crystalline or amorphous particles or a mixture thereof is in the range 10 nm to 2000 nm, 10 nm to 1500 nm, 10 nm to 1000 nm, 10 nm to 800 nm, 10 nm to 750 nm; 10 nm to 600 nm, 10 nm to 500 nm, 10 nm to 400 nm, 10 nm to 300 nm, 10 nm to 250 nm, 10 nm to 200 nm, or 10 nm to 100 nm.

Dosage Form Examples

Example A

| Ingredient Name | | | Dosage Form A1 | | Dosage Form A2 | |
|---|---|---|---|---|---|---|
| | | | % w/w | mg/unit | % w/w | mg/unit |
| Testosterone Undecanoate | | | 10-20 | 105-125 | 10-15 | 105-125 |
| Pharmaceutically acceptable carriers | Lipophilic additives* | e.g. Castor oil | — | — | 48-55 | 450-560 |
| | | e.g. Oleic acid | 80-90 | 740-895 | — | — |
| | | e.g. Propylene glycol monolaurate | — | — | 30-40 | 300-375 |
| | Other additives** (e.g. antioxidant, solidifier, etc) | | 0-10 | 0-100 | 0-12 | 0-120 |
| Total | | | 100 | 840-1050 | 100 | 850-1050 |

*Lipophilic additives used in these compositions (e.g. castor oil, oleic acid, and propylene glycol monolaurate) can be replaced with other lipophilic additives or combinations described in the above contexts. This can be applied to all other examples.
**Other additives exemplified as antioxidant or solidifier in these compositions can be replaced with different other additives or combinations described in the above contexts. This can be applied to all other examples.

Example B

| Ingredient Name | | | Dosage Form B1 | | Dosage Form B2 | | Dosage Form B3 | |
|---|---|---|---|---|---|---|---|---|
| | | | % w/w | mg/unit | % w/w | mg/unit | % w/w | mg/unit |
| Testosterone Undecanoate | | | 13-17 | 105-125 | 28-32 | 210-245 | 18-22 | 105-245 |
| Pharmaceutically acceptable carriers | Lipophilic additives* | Mono/di-glyceride1 (e.g. Glyceryl monolinoleate) | 60-65 | 435-530 | — | — | — | — |
| | | Mono/di-glyceride2 (e.g. Glyceryl distearate) | — | — | 4-8 | 50-75 | — | — |
| | | Fatty acid1 (e.g. Oleic acid) | — | — | 50-60 | 400-450 | 45-55 | 260-650 |
| | | Fatty acid2 (e.g. Stearic acid) | — | — | 2-6 | 25-40 | — | — |
| | | Triglyceride1 (e.g. Borage oil) | — | — | — | — | 8-12 | 45-130 |
| | | Triglyceride2 (e.g. Peppermint oil) | — | — | — | — | 2-4 | 10-35 |
| | Hydrophilic additives** (e.g. Polyoxyl 40 hydrogenated castor oil) | | 13-17 | 100-140 | 2-6 | 25-40 | 14-18 | 60-225 |

-continued

|  |  | Dosage Form B1 | | Dosage Form B2 | | Dosage Form B3 | |
|---|---|---|---|---|---|---|---|
| Ingredient Name | | % w/w | mg/unit | % w/w | mg/unit | % w/w | mg/unit |
| Other additives*** | Solidifiers (e.g. PEG) | 4-8 | 40-55 | — | — | — | — |
| | Antioxidant | 0-0.3 | 0-2.5 | 0-0.3 | 0-2.5 | 0-0.3 | 0-2.5 |
| Total | | 100 | 680-850 | 100 | 720-850 | 100 | 500-1250 |

*Lipophilic additives used in these compositions can be replaced with other lipophilic additives or combinations described in the above contexts. This can be applied to all other examples.
*Hydrophilic additives used in these compositions (e.g. polyoxyl 40 hydrogenated castor oil) can be replaced with other hydrophilic additives or combinations described in the above contexts. This can be applied to all other examples.
***Other additives exemplified as solidifier and antioxidant in these compositions can be replaced with different other additives or combinations described in the above contexts. This can be applied to all other examples.

Example C

| | | | Dosage Form C1 | | Dosage Form C2 | | Dosage Form C3 | |
|---|---|---|---|---|---|---|---|---|
| | | Ingredient Name | % w/w | mg/unit | % w/w | mg/unit | % w/w | mg/unit |
| | | Testosterone Undecanoate | 10-15 | 105-125 | 10-15 | 105-125 | 10-15 | 105-125 |
| Pharmaceutically acceptable carriers | Lipophilic additives* | Triglyceride (e.g. Castor oil) | 22-28 | 220-290 | — | — | — | — |
| | | Fatty acid (e.g. Oleic acid) | — | — | 24-30 | 230-300 | 24-30 | 230-300 |
| | | Mono/di-glyceride derivative (e.g. Propylene glycol monolaurate) | 15-18 | 145-195 | — | — | — | — |
| | | Mono/di-glyceride (e.g. Glyceryl distearate) | — | — | — | — | 12-15 | 110-150 |
| | | Monoglyceride (e.g. Glyceryl monooleate) | — | — | 14-18 | 135-180 | 5-10 | 65-110 |
| | | Glyceride derivative (e.g. Oleoyl polyoxyl-6 glycerides) | 10-15 | 100-145 | 10-15 | 100-145 | 4-6 | 42-60 |
| | | Lipophilic surfactant (e.g. Lecithin) | 0.5-1.5 | 5-15 | 0.5-1.5 | 5-15 | 0.5-1.5 | 5-15 |
| | | Lipophilic surfactant (e.g. Phytosterol) | 1-3 | 15-30 | 1-3 | 15-30 | 1-3 | 15-30 |
| | Hydrophilic additives** | e.g. Polyoxyl 40 hydrogenated castor oil | 25-35 | 250-345 | 6-12 | 75-125 | 6-12 | 75-125 |
| | | e.g. Polysorbate 80 | — | — | 18-22 | 170-225 | 18-22 | 170-225 |
| | | e.g. D-alpha-tocopherol | — | — | 1-3 | 12-25 | 1-3 | 12-25 |
| | Other additives*** | Control release agent | 0.5-1.5 | 5-15 | 0.5-1.5 | 5-15 | 0.5-1.5 | 5-15 |
| | | Antioxidant | 0-0.3 | 0-1.0 | 0-0.3 | 0-1.0 | 0-0.3 | 0-10 |
| | | Total | 100 | 850-1150 | 100 | 850-1150 | 100 | 850-1150 |

*Lipophilic additives used in these compositions can be replaced with other lipophilic additives or combinations described in the above contexts. This can be applied to all other compositions.
*Hydrophilic additives used in these compositions can be replaced with other hydrophilic additives or combinations described in the above contexts. This can be applied to all other compositions.
***Other additives used in these compositions can be replaced with different other additives or combinations described in the above contexts. This can be applied to all other compositions.

Examples of Dosing Regimens:

Non-limiting examples of dosing regimens for oral TT with dosage forms containing compositions of this invention comprising TU are described below:

Fixed Dose Dosing Regimen Examples Based on Study Described Below for Estimated or Actual $C_{max}$ Values (Administered with Food with at Least 10 g of Fat)

| Category | Regimen # | TU Dose (mg) | Cmax > 1500 ng/dL | | Cmax > 1800 ng/dL | | Cmax > 2500 ng/dL | |
|---|---|---|---|---|---|---|---|---|
| | | | <20% patients | <15% patients | <10% patients | <5% patients | <2% patients | none of patients |
| TID-equal dose | 1 | 75/75/75 | Yes | Yes | Yes | Yes | Yes | Yes |
| | 2 | 112/112/112 | Yes | Yes | Yes | Yes | Yes | Yes |
| | 3 | 125/125/125 | Yes | Yes | Yes | Yes | Yes | Yes |
| | 4 | 150/150/150 | Yes | Yes | Yes | Yes | Yes | Yes |
| | 5 | 188/188/188 | Yes | Yes | Yes | Yes | Yes | Yes |
| | 6 | 225/225/225 | Yes | No | Yes | No | Yes | No |
| | 7 | 237/237/237 | Yes | No | Yes | No | No | No |
| | 8 | 250/250/250 | No | No | No | No | No | No |
| BID-equal dose (AM/PM) | 9 | 75/75 | Yes | Yes | Yes | Yes | Yes | Yes |
| | 10 | 150/150 | Yes | Yes | Yes | Yes | Yes | Yes |
| | 11 | 215/215 | Yes | Yes | Yes | Yes | Yes | Yes |
| | 12 | 225/225 | Yes | Yes | Yes | Yes | Yes | Yes |
| | 13 | 237/237 | Yes | Yes | Yes | Yes | Yes | Yes |
| | 14 | 250/250 | Yes | No | Yes | Yes | Yes | Yes |
| | 15 | 265/265 | Yes | No | Yes | No | Yes | No |
| | 16 | 300/300 | No | No | Yes | No | Yes | No |
| BID-different dose (AM/PM) | 17 | 75/225 | Yes | Yes | Yes | Yes | Yes | Yes |
| | 18 | 75/300 | Yes | Yes | Yes | No | Yes | No |
| | 19 | 150/225 | Yes | Yes | Yes | Yes | Yes | Yes |
| | 20 | 225/150 | Yes | Yes | Yes | Yes | Yes | Yes |
| | 21 | 225/300 | No | No | Yes | No | Yes | No |
| | 22 | 300/75 | Yes | No | Yes | No | Yes | No |
| | 23 | 300/150 | Yes | No | Yes | No | Yes | No |
| | 24 | 300/225 | No | No | Yes | No | Yes | No |

Fixed Dose Dosing Regimen Examples Based on Study Described Below for Estimated or Actual $C_{avg}$ (Administered with Food with at Least 10 g of Fat)

| Category | Regimen # | TU Dose (mg) | Cavg >300 ng/dL | |
|---|---|---|---|---|
| | | | ≥80% patients | ≥75% patients |
| TID-equal dose | 1 | 75/75/75 | No | No |
| | 2 | 112/112/112 | No | No |
| | 3 | 125/125/125 | No | No |
| | 4 | 150/150/150 | Yes | Yes |
| | 5 | 188/188/188 | Yes | Yes |
| | 6 | 225/225/225 | Yes | Yes |
| | 7 | 237/237/237 | Yes | Yes |
| | 8 | 250/250/250 | Yes | Yes |
| BID-equal dose (AM/PM) | 9 | 75/75 | No | No |
| | 10 | 150/150 | No | No |
| | 11 | 215/215 | No | Yes |
| | 12 | 225/225 | Yes | Yes |
| | 13 | 237/237 | Yes | Yes |
| | 14 | 250/250 | Yes | Yes |
| | 15 | 265/265 | Yes | Yes |
| | 16 | 300/300 | Yes | Yes |
| BID-different dose (AM/PM) | 17 | 75/225 | No | No |
| | 18 | 75/300 | No | No |
| | 19 | 150/225 | No | No |
| | 20 | 225/150 | No | Yes |
| | 21 | 225/300 | Yes | Yes |
| | 22 | 300/75 | No | No |
| | 23 | 300/150 | Yes | Yes |
| | 24 | 300/225 | Yes | Yes |

The dosage form from Example B of Composition 4 with dosing regimen (Regimen #9-16) of dosing category BID-equal dose with daily dose range 150-600 mg were used for a Clinic Study of Testosterone Therapy for hypogonadal males.

The clinical study was a randomized double-blind, placebo-controlled dose escalating study of the safety, efficacy, tolerability, and pharmacokinetics of testosterone therapy in hypogonadal males. This clinic study was a single and multiple, ascending-dose study that was designed to determine the optimal starting, titration (if appropriate), or single fixed dose for safety and efficacy targeted by the US FDA. The study also verified the time for testosterone levels to reach steady state and identified a suitable fixed dose dosing regimen that satisfies an unmet need for safety and efficacy for oral TT.

This study was carried out with conditions of a single-center, randomized, double-blind, placebo-controlled, ascending multiple-dose, and serial-group in adult hypogonadal male subjects. The objectives of this study were:

a) To assess the safety, efficacy, and tolerability of escalating single and multiple oral doses of TU dosage forms in hypogonadal males b) To determine the pharmacokinetics (PK) of testosterone (T), DHT, TU, DHTU, and estradiol (E2) after single and multiple oral doses of TU dosage forms in hypogonadal males C) To identify a fixed dose dosing regimen satisfying US FDA targets, without needing to titrate, for restoring serum T levels in hypogonadal males to the normal T range.

The following sections summarize the some relevant elements of the study and pertinent clinical pharmacology results.

The dosing regimen for this clinical study ranged from 150 mg daily dose (75 mg BID dose) to 600 mg daily dose (300 mg BID dose). Observed pharmacokinetic parameters (T, DHT, TU, DHTU, and E2) after single and multiple oral doses of TU dosage forms in the patients were recorded in connection with each daily dose listed in the report. Further analysis to identify a fixed dose dosing regimen that does not need titration for safety and efficacy was carried out based on the criteria targeted by US FDA. For example, the pharmacokinetic parameters of T level after administration of the dosing regimens for 225 mg BID-equal dose were measured and analyzed according to the criteria targeted by US FDA as T $C_{avg}$/day >300 ng/dL in greater than 75% of patients 225 mg BID-equal dose dosing regimen resulted in 83.5% of patients with T $C_{avg}$/day >300 ng/dL T $C_{max}$/dose <1,500 ng/dL in greater than 85% of patients 225 mg BID-equal dose dosing regimen resulted in 89.9% of patients with T $C_{max}$/dose <1,500 ng/dL The overall analyzed results of this clinical study were plotted according to % of patients for safety ($C_{max}$<1,500 ng/dL) and efficacy ($C_{avg}$>300 ng/dL) with a variety of dosing regimens. The results are shown in the table below. Note that only doses that were multiples of 75 mg were tested in the clinical study, the results predicted for the other doses are estimated from these values.

Clinical Trial Results for % Patients for the $C_{avg}$ Criteria with Various Daily Dose (or BID)

| Daily dose (mg) | Each BID dose (mg) | % with Cavg/day >300 ng/dL |
| --- | --- | --- |
| 410 | 205 | 71.5 |
| 420 | 210 | 74.9 |
| 430* | 215 | 77.6 |
| 438 | 219 | 80.0 |
| 450 | 225 | 83.5 |
| 460 | 230 | 85.6 |
| 474 | 237 | 88.9 |
| 480 | 240 | 90.0 |
| 490 | 245 | 91.7 |
| 500 | 250 | 93.0 |
| 518 | 259 | 95.2 |

*Daily doses with bold letters satisfy the criteria of % patients >75% for Cavg/day >300 ng/dL.

Clinical Trial Results for % Patients for the $C_{max}$ Criteria with Various Daily Dose (or BID)

| Daily dose (mg) | Each BID dose (mg) | % with Cmax/dose <1,500 ng/dL |
| --- | --- | --- |
| 410* | 205 | 93.7 |
| 420 | 210 | 92.8 |
| 430 | 215 | 92.1 |
| 438 | 219 | 91.2 |
| 450 | 225 | 89.9 |
| 460 | 230 | 88.9 |
| 474 | 237 | 86.8 |
| 480 | 240 | 86.1 |
| 490 | 245 | 84.6 |
| 500 | 250 | 83.2 |
| 518 | 259 | 80.0 |

*Daily doses in bold satisfy the criteria of % patients >85% for Cmax/dose <1,500 ng/dL.

In conclusion, these Examples show that a fixed dose dosing regimen with no need to titrate (or adjust) the dose having a dose in the range of from 430 mg TU daily dose (215 mg BID-equal dose) to 480 mg TU daily dose (240 mg BID-equal dose), can satisfy US FDA T level targets for safety and efficacy without titration.

Those skilled in the art will appreciate that the concepts, specific embodiments, and Examples disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of restoring serum testosterone levels to a normal eugonadal range in a male having a condition associated with a deficiency or absence of endogenous testosterone, comprising orally administering a pharmaceutical composition comprising a therapeutically effective amount of testosterone undecanoate (TU) and an additive as a hard or soft capsule in a unit dosage form providing 112.5 mg or 225 mg of TU in a fixed dose administration regimen of twice daily administration with food to provide a total daily dose of TU of from 420-500 mg, said method further comprising discontinuing said orally administering when said male consistently has serum testosterone concentrations above about 1040-1100 ng/dl measured about 8-9 hours after a single dose administration of said pharmaceutical composition, wherein said serum testosterone concentrations are measured on at least two or more separate occasions with a gap of at least 24 hours.

2. A method of restoring daily average serum testosterone ($C_{avg}$) to a normal eugonadal range in at least 75% of males in a population having a condition associated with a deficiency or absence of endogenous testosterone, comprising oral administration of an oral dosage form comprising a therapeutically effective amount of testosterone undecanoate (TU) and an additive as a hard or soft capsule in a unit dosage form providing 112.5 mg or 225 mg of TU in a fixed dose administration regimen of twice daily with food to provide a total daily dose of TU of from 420-500 mg, said method further comprising discontinuing said oral administration when said male consistently has serum testosterone concentrations above about 1040-1100 ng/dl measured about 8-9 hours after a single dose administration of said pharmaceutical composition, wherein said serum testosterone concentrations are measured on at least two or more separate occasions with a gap of at least 24 hours.

3. A method of treating a condition associated with a deficiency or absence of endogenous testosterone in a male patient, comprising: orally administering a composition comprising testosterone undecanoate (TU) and an additive as a hard or soft capsule in a unit dosage form providing 112.5 or 225 mg of TU in a in a fixed dose dosing regimen of twice daily with food to provide a total daily dose of TU of from 420-500 mg TU, said method further comprising discontinuing said orally administering when said male consistently has serum testosterone concentrations above about 1040-1100 ng/dl measured about 8-9 hours after a single dose administration of said pharmaceutical composition, wherein said serum testosterone concentrations are measured on at least two or more separate occasions with a gap of at least 24 hours.

4. The method of claim 3, further comprising determining a serum testosterone level of said male patient after initiation of administration of TU.

5. The method of claim 3, further comprising determining a serum testosterone level of said male after initiation of TU administration, wherein unacceptably low serum testosterone levels after reaching a steady state indicates an advised discontinuation of therapy.

6. The method of claim 3, wherein the fixed dose provides about 450 mg testosterone undecanoate per day.

7. The method of claim 3, wherein the fixed dose provides safe and efficacious testosterone replacement therapy.

8. The method of claim 3, wherein the fixed dose provides about 225 mg testosterone undecanoate per dose.

9. The method of claim 3, further comprising determining a total serum testosterone concentration, wherein a total serum testosterone concentration that is consistently below 300 ng/dL indicates an advised discontinuation of therapy.

10. The method of claim 3, further comprising assessing discontinuation criteria at steady state.

11. The method of claim 3, further comprising assessing discontinuation criteria at steady state by measuring serum testosterone concentrations.

12. The method of claim 3, further comprising determining a hematocrit or PSA level for the patient, wherein an unacceptably high hematocrit level or an unacceptably high PSA level indicates an advised discontinuation of therapy.

13. The method of claim 3, wherein administration of the fixed dose of TU in the fixed dose dosing regimen provides ≥75% of patients in a population with an average serum T ($C_{avg}$) within a normal range, wherein the population comprises a group of at least 20 individuals.

14. The method of claim 3, wherein administration of the fixed dose of TU in the fixed dose dosing regimen provides ≥65% of patients in a population with an average serum T ($C_{avg}$) within a normal range, wherein the population comprises a group of at least 20 individuals.

15. The method of claim 3, wherein administration of the fixed dose of TU in the fixed dose dosing regimen provides ≥75% of patients in a population with a $C_{max}$<1500 ng/dL, wherein the population comprises a group of at least 20 individuals.

16. The method of claim 3, wherein administration of the fixed dose of TU in the fixed dose dosing regimen provides ≥90% of patients in a population with a $C_{max}$<1800 ng/dL, wherein the population comprises a group of at least 20 individuals.

17. The method of claim 3, wherein administration of the fixed dose of TU in the fixed dose dosing regimen provides ≥95% of patients in a population with a $C_{max}$<2500 ng/dL, wherein the population comprises a group of at least 20 individuals.

* * * * *